United States Patent
Möckel et al.

(10) Patent No.: US 6,806,068 B1
(45) Date of Patent: Oct. 19, 2004

(54) NUCLEOTIDE SEQUENCES WHICH ENCODE THE PFK GENE

(75) Inventors: Bettina Möckel, Düsseldorf (DE); Walter Pfefferle, Halle (DE)

(73) Assignee: Degussa AG Dusseldorf (DE)

( * ) Notice: Subject to any disclaimer, the term of this patent is extended or adjusted under 35 U.S.C. 154(b) by 364 days.

(21) Appl. No.: 09/715,040

(22) Filed: Nov. 20, 2000

(30) Foreign Application Priority Data

Nov. 23, 1999 (DE) .......................... 199 56 131

(51) Int. Cl.⁷ .................. C12P 13/04; C12P 13/08; C07H 21/04; C12N 1/20; C12N 15/00
(52) U.S. Cl. ................ 435/106; 435/115; 435/320.1; 435/252.3; 435/252.32; 536/23.1; 536/23.2; 536/23.7; 536/24.32
(58) Field of Search ............... 536/23.2, 24.3, 536/23.1, 23.7, 24.32; 435/320.1, 194, 106, 115, 252.3, 252.32

(56) References Cited

FOREIGN PATENT DOCUMENTS

| EP | 1 010 755 A | 6/2000 |
|---|---|---|
| EP | 0 108 790 | 6/2001 |
| WO | WO 01 00844 A | 1/2001 |

OTHER PUBLICATIONS

Branden et al. "Introduction to Protein Structure", Garland Publishing Inc., New York, 1991.*
Witkowski et al. (1999) Biochemistry 38:11643–11650.*
Database WPI, Section Ch, Week 198824, Derwent Publications Ltd., London, GB; Class B05, AN 1988–164726, XP002162778 & JP 63 102692 A, May 7, 1988.
Database EMBL, Wells et al., "Triticum aestivum heat shock protein 101 kDa (HSP101) mRNA, complete cds.", Dec. 1998, XP002162775.
Database EMBL, Orchard et al., "E. coli fruK gene for 1–phosphofructokinase", Sep. 1991, XP002162776.
Database EMBL, Orchard et al., "1–phosphofructokinase (EC 2.7.1.56) (Fructose 1–phosphate kinase", XP002162777 Nov. 1, 1991.
Kiyoshi Nakayama: "Microorganisms in amino acid fermentation" 1972, Society of Fermentation Technology, Japan, XP002163104.

* cited by examiner

*Primary Examiner*—David Steadman
(74) *Attorney, Agent, or Firm*—Pillsbury Winthrop LLP

(57) ABSTRACT

The present invention is directed to nucleotide sequences coding for phosphofructokinase which have been derived from *Corynebacterium glutamicum*. The invention also encompasses methods for fermentatively producing amino acids using bacteria in which phosphofructokinase activity has been enhanced

8 Claims, 1 Drawing Sheet

Figure 1: Plasmid pZ-pfkex
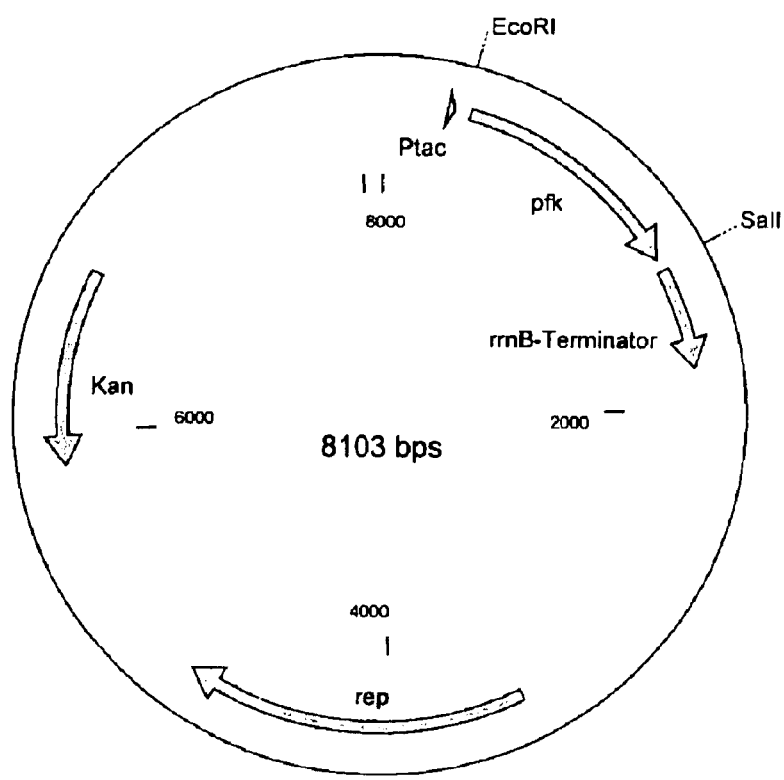

SEQUENCE LISTING

<160> NUMBER OF SEQ ID NOS: 4

<210> SEQ ID NO 1
<211> LENGTH: 1120
<212> TYPE: DNA
<213> ORGANISM: Corynebacterium glutamicum
<220> FEATURE:
<221> NAME/KEY: CDS
<222> LOCATION: (68)..(1057)

<400> SEQUENCE: 1

```
ttgttaccga tgaccacacg ctagattttc cagttttgcc cgaccacaac tttcaggtgg      60
taacccc atg atc atc aca ttc acc cca aac ccg agt att gat tcc acg      109
        Met Ile Ile Thr Phe Thr Pro Asn Pro Ser Ile Asp Ser Thr
         1               5                  10 ctg tcg ctc ggc gaa gag ctc tcc cgt gga tcc gtc caa cga ctt gat      157
Leu Ser Leu Gly Glu Glu Leu Ser Arg Gly Ser Val Gln Arg Leu Asp
 15              20                  25                  30 tcc gtc acc gct gtc gca ggt ggt aaa ggc atc aat gtc gcc cac gct      205
Ser Val Thr Ala Val Ala Gly Gly Lys Gly Ile Asn Val Ala His Ala
                 35                  40                  45 gtc ttg ctt gcg ggc ttt gaa acc ttg gct gtg ttc cca gcc ggc aag      253
Val Leu Leu Ala Gly Phe Glu Thr Leu Ala Val Phe Pro Ala Gly Lys
             50                  55                  60 ctc gac ccc ttc gtc cca ctg gtc cgc gac atc ggc ttg ccc gtg gaa      301
Leu Asp Pro Phe Val Pro Leu Val Arg Asp Ile Gly Leu Pro Val Glu
         65                  70                  75 act gtt gtg atc aac aag aac gtc cgc acc aac acc aca gtc acc gaa      349
Thr Val Val Ile Asn Lys Asn Val Arg Thr Asn Thr Thr Val Thr Glu
 80                  85                  90 ccg gac ggc acc acc acc aag ctc aac ggc ccc ggc gcg ccg ctc agc      397
Pro Asp Gly Thr Thr Thr Lys Leu Asn Gly Pro Gly Ala Pro Leu Ser
 95                 100                 105                 110 gag cag aag ctc cgt agc ttg gaa aag gtg ctt atc gac gcg ctc cgc      445
Glu Gln Lys Leu Arg Ser Leu Glu Lys Val Leu Ile Asp Ala Leu Arg
                115                 120                 125 ccc gaa gtc acc tgg gtt gtc ctg gcg ggc tcg ctg cca cca ggg gca      493
Pro Glu Val Thr Trp Val Val Leu Ala Gly Ser Leu Pro Pro Gly Ala
            130                 135                 140 cca gtt gac tgg tac gcg cgt ctc acc gcg ttg atc cat tca gca cgc      541
Pro Val Asp Trp Tyr Ala Arg Leu Thr Ala Leu Ile His Ser Ala Arg
        145                 150                 155 cct gac gtt cgc gtg gct gtc gat acc tca gac aag cca ctg atg gcg      589
Pro Asp Val Arg Val Ala Val Asp Thr Ser Asp Lys Pro Leu Met Ala
    160                 165                 170 ttg ggc gag agc ttg gat aca cct ggc gct gct ccg aac ctg att aag      637
Leu Gly Glu Ser Leu Asp Thr Pro Gly Ala Ala Pro Asn Leu Ile Lys
175                 180                 185                 190 cca aat ggt ctg gaa ctg ggc cag ctg gct aac act gat ggt gaa gag      685
Pro Asn Gly Leu Glu Leu Gly Gln Leu Ala Asn Thr Asp Gly Glu Glu
                195                 200                 205 ctg gag gcg cgt gct gcg caa ggc gat tac gac gcc atc atc gca gct      733
Leu Glu Ala Arg Ala Ala Gln Gly Asp Tyr Asp Ala Ile Ile Ala Ala
            210                 215                 220 gcg gac gta ctg gtt aac cgt ggc atc gaa cag gtg ctt gtc acc ttg      781
Ala Asp Val Leu Val Asn Arg Gly Ile Glu Gln Val Leu Val Thr Leu
        225                 230                 235 ggt gcc gca gga gcg gtg ttg gtc aac gca gaa ggt gcg tgg act gct      829
Gly Ala Ala Gly Ala Val Leu Val Asn Ala Glu Gly Ala Trp Thr Ala
    240                 245                 250
```

```
act tct cca aag att gat gtt gta tcc acc gtt gga gct gga gac tgt      877
Thr Ser Pro Lys Ile Asp Val Val Ser Thr Val Gly Ala Gly Asp Cys
255                 260                 265                 270 gct ctt gca ggt ttt gtt atg gca cgt tcc cag aag aaa aca ctg gag      925
Ala Leu Ala Gly Phe Val Met Ala Arg Ser Gln Lys Lys Thr Leu Glu
                275                 280                 285 gaa tct ctg ctg aat gcc gtg tct tac ggc tcg act gcg gcg tct ctt      973
Glu Ser Leu Leu Asn Ala Val Ser Tyr Gly Ser Thr Ala Ala Ser Leu
            290                 295                 300 cct ggc act acc att cct cgt cct gac caa ctc gcc aca gct ggt gca     1021
Pro Gly Thr Thr Ile Pro Arg Pro Asp Gln Leu Ala Thr Ala Gly Ala
        305                 310                 315 acg gtc acc caa gtc aaa gga ttg aaa gaa tca gca tgaatagcgt          1067
Thr Val Thr Gln Val Lys Gly Leu Lys Glu Ser Ala
    320                 325                 330 aaataattcc tcgcttgtcc ggctggatgt cgatttcggc gactccacca cgg          1120

<210> SEQ ID NO 2
<211> LENGTH: 330
<212> TYPE: PRT
<213> ORGANISM: Corynebacterium glutamicum

<400> SEQUENCE: 2

Met Ile Ile Thr Phe Thr Pro Asn Pro Ser Ile Asp Ser Thr Leu Ser
1               5                   10                  15

Leu Gly Glu Glu Leu Ser Arg Gly Ser Val Gln Arg Leu Asp Ser Val
            20                  25                  30

Thr Ala Val Ala Gly Gly Lys Gly Ile Asn Val Ala His Ala Val Leu
        35                  40                  45

Leu Ala Gly Phe Glu Thr Leu Ala Val Phe Pro Ala Gly Lys Leu Asp
    50                  55                  60

Pro Phe Val Pro Leu Val Arg Asp Ile Gly Leu Pro Val Glu Thr Val
65                  70                  75                  80

Val Ile Asn Lys Asn Val Arg Thr Asn Thr Thr Val Thr Glu Pro Asp
                85                  90                  95

Gly Thr Thr Thr Lys Leu Asn Gly Pro Gly Ala Pro Leu Ser Glu Gln
            100                 105                 110

Lys Leu Arg Ser Leu Glu Lys Val Leu Ile Asp Ala Leu Arg Pro Glu
        115                 120                 125

Val Thr Trp Val Val Leu Ala Gly Ser Leu Pro Pro Gly Ala Pro Val
    130                 135                 140

Asp Trp Tyr Ala Arg Leu Thr Ala Leu Ile His Ser Ala Arg Pro Asp
145                 150                 155                 160

Val Arg Val Ala Val Asp Thr Ser Asp Lys Pro Leu Met Ala Leu Gly
                165                 170                 175

Glu Ser Leu Asp Thr Pro Gly Ala Ala Pro Asn Leu Ile Lys Pro Asn
            180                 185                 190

Gly Leu Glu Leu Gly Gln Leu Ala Asn Thr Asp Gly Glu Glu Leu Glu
        195                 200                 205

Ala Arg Ala Ala Gln Gly Asp Tyr Asp Ala Ile Ile Ala Ala Ala Asp
    210                 215                 220

Val Leu Val Asn Arg Gly Ile Glu Gln Val Leu Val Thr Leu Gly Ala
225                 230                 235                 240

Ala Gly Ala Val Leu Val Asn Ala Glu Gly Ala Trp Thr Ala Thr Ser
                245                 250                 255
```

-continued

```
Pro Lys Ile Asp Val Val Ser Thr Val Gly Ala Gly Asp Cys Ala Leu
            260             265             270

Ala Gly Phe Val Met Ala Arg Ser Gln Lys Lys Thr Leu Glu Glu Ser
        275             280             285

Leu Leu Asn Ala Val Ser Tyr Gly Ser Thr Ala Ala Ser Leu Pro Gly
    290             295             300

Thr Thr Ile Pro Arg Pro Asp Gln Leu Ala Thr Ala Gly Ala Thr Val
305             310             315             320

Thr Gln Val Lys Gly Leu Lys Glu Ser Ala
            325             330

<210> SEQ ID NO 3
<211> LENGTH: 31
<212> TYPE: DNA
<213> ORGANISM: PCR primer

<400> SEQUENCE: 3
gatctagaat tcaactttca ggtggtaacc c                              31

<210> SEQ ID NO 4
<211> LENGTH: 31
<212> TYPE: DNA
<213> ORGANISM: PCR primer

<400> SEQUENCE: 4
gatctagtcg accggacaag cgaggaatta t                              31
```

NUCLEOTIDE SEQUENCES WHICH ENCODE THE PFK GENE

This application claims priority from German Application No. 199 56 131.1, filed on Nov. 23, 1999, the subject matter of which is hereby incorporated herein by reference.

BACKGROUND OF THE INVENTION

1. Field of the Invention

The invention provides nucleotide sequences which encode the pfk gene and a process for the fermentative preparation of amino acids, in particular L-lysine, using coryneform bacteria in which the pfk gene is enhanced.

2. Background Information

Amino acids, in particular L-lysine, are used in human medicine and in the pharmaceuticals industry, but in particular in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the processes can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites, such as, for example, the lysine analogue S-(2-aminoethyl)-cysteine, or are auxotrophic for metabolites of regulatory importance and produce L-amino acids, such as, for example, L-lysine, are obtained in this manner.

Recombinant DNA techniques have also been employed for some years for improving Corynebacterium strains which produce amino acids, by amplifying individual amino acid biosynthesis genes and investigating the effects of such changes on the amino acid production. Review articles on this subject are to be found, inter alia, in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)) and Sahm et al. (Annuals of the New York Academy of Science 782, 25–39 (1996)).

SUMMARY OF THE INVENTION

Object of the Invention

It is an object of the invention to provide new means for improved fermentative preparation of amino acids, in particular L-lysine.

Description of the Invention

Amino acids, in particular L-lysine, are used in human medicine, in the pharmaceuticals industry and in particular in animal nutrition. There is therefore a general interest in providing new improved processes for the preparation of amino acids, in particular L-lysine.

When L-lysine or lysine are mentioned in the following, not only the base but also the salts, such as, for example, lysine monohydrochloride or lysine sulfate, are also meant.

The invention provides an isolated polynucleotide from coryneform bacteria, comprising a polynucleotide sequence chosen from the group consisting of a) a polynucleotide which is at least 70% identical to a polynucleotide which encodes a polypeptide which comprises the amino acid sequence of SEQ ID NO:2, b) a polynucleotide which encodes a polypeptide which comprises an amino acid sequence which is at least 70% identical to the amino acid sequence of SEQ ID NO:2, c) a polynucleotide which is complementary to the polynucleotides of a) or b), and d) a polynucleotide comprising at least 15 successive nucleotides of the polynucleotide sequence of a), b) or c).

In a preferred embodiment, the invention also provides the polynucleotide with the features described above, preferably being a DNA which is capable of replication, comprising:

(i) the nucleotide sequence shown in SEQ ID NO:1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide with the aforementioned features, comprising the nucleotide sequence as shown in SEQ ID NO:1, a polynucleotide with the aforementioned features, which encodes a polypeptide which comprises the amino acid sequence as shown in SEQ ID NO:2, a vector containing the polynucleotide with features a)-d) above, in particular a shuttle vector or plasmid vector and coryneform bacteria serving as the host cell, which contain the vector.

The invention also provides polynucleotides which substantially comprise a polynucleotide sequence, which are obtainable by screening by means of hybridization of a corresponding gene library, which comprises the complete gene with the polynucleotide sequence corresponding to SEQ ID NO:1, with a probe which comprises the sequence of the polynucleotide mentioned, according to SEQ ID no. 1 or a fragment thereof, and isolation of the DNA sequence mentioned.

Polynucleotide sequences according to the invention are suitable as hybridization probes for RNA, cDNA and DNA, in order to isolate, in the full length, CDNA which code for phosphofructokinase and to isolate those cDNA or genes which have a high similarity of sequence with that of the phosphofructokinase gene.

Polynucleotide sequences according to the invention are furthermore suitable as primers for the preparation of DNA of genes which code for phosphofructokinase by the polymerase chain reaction (PCR).

Such oligonucleotides which serve as probes or primers comprise at least 30, preferably at least 20, very particularly preferably at least 15 successive nucleotides. oligonucleotides which have a length of at least 40 or 50 nucleotides are also suitable.

"Isolated" means separated from its natural environment.

"Polynucleotide" generally relates to polyribonucleotides and polydeoxyribonucleotides, wherein the RNA or DNA may be modified or unmodified.

"Polypeptides" is understood as meaning peptides or proteins which comprise two or more amino acids bonded via peptide bonds.

The polypeptides according to the invention include a polypeptide according to SEQ ID NO:2, in particular those with the biological activity of phosphofructokinase, and also those which are at least 70% identical to the polypeptide according to SEQ ID NO:2, and preferably are at least 80% identical, and most preferably 90% to 95% identical to the polypeptide according to SEQ ID NO:2 and have the activity mentioned.

The invention also provides a process for the fermentative preparation of amino acids, in particular L-lysine, using coryneform bacteria which in particular already produce an amino acid, and in which the nucleotide sequences which code for the pfk gene are enhanced, in particular overexpressed.

The term "enhancement" in this connection describes the increase in the intracellular activity of one or more enzymes in a microorganism which are encoded by the corresponding DNA, for example by increasing the number of copies of the gene or genes, using a potent promoter or using a gene which encodes a corresponding enzyme having a high activity, and optionally combining these measures.

The microorganisms provided by the present invention can be used to prepare L-amino acids, in particular L-lysine, from glucose, sucrose, lactose, fructose, maltose, molasses, starch, cellulose or from glycerol and ethanol. They can be representatives of coryneform bacteria, in particular of the genus Corynebacterium. Of the genus Corynebacterium, the species *Corynebacterium glutamicum*, which is known among experts for its ability to produce L-amino acids, is particularly useful.

Suitable strains of the genus Corynebacterium, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
Brevibacterium divaricatumATCC14020 and L-lysine-producing mutants or strains prepared therefrom, such as, for example

*Corynebacterium glutamicum* FERM-P 1709
*Brevibacterium flavum* FERM-P 1708
Brevibacterium lactofermentumFERM-P 1712
*Corynebacterium glutamicum* FERM-P 6463
*Corynebacterium glutamicum* FERM-P 6464 and
*Corynebacterium glutamicum* DSM5715.

The inventors have succeeded in isolating the new pfk gene of *C. glutamicum* which codes for the enzyme phosphofructokinase.

To isolate the pfk gene or also other genes of *C. glutamicum*, a gene library of this microorganism is first constructed in *E. coli*. The construction of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) or the handbook by Sambrook et al.: Molecular Cloning, A Laboratory Manual (Cold Spring Harbor Laboratory Press, 1989) may be mentioned as examples. A well-known gene library is that of the *E. coli* K-12 strain W3110 constructed in λ vectors by Kohara et al. (Cell 50, 495–508 (1987)). Bathe et al. (Molecular and General Genetics, 252:255–265, 1996) describe a gene library of *C. glutamicum* ATCC13032, which was constructed with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326)) (1992)) in turn describe a gene library of *C. glutamicum* ATCC13032 using the cosmid pHC79 (Hohn and Collins, Gene 11, 291–298 (1980)). To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DHαmcr, which has been described by Grant et al. (Proceedings of the National Academy of Sciences USA, 87 (1990) 4645–4649). The long DNA fragments cloned with the aid of cosmids can then in turn be subcloned in the usual vector suitable for sequencing and then sequenced, as is described, for example, by Sanger et al. (Proceedings of the National Academy of Sciences of the United States of America, 74:5463–5467, 1977).

The new DNA sequence of *C. glutamicum* which encodes the pfk gene and which, as SEQ ID NO:1, is a constituent of the present invention, was obtained in this manner. The amino acid sequence of the corresponding protein has furthermore been derived from the present DNA sequence by the methods described above. The resulting amino acid sequence of the pfk gene product is shown in SEQ ID NO:2.

Coding DNA sequences which arise from SEQ ID NO:1 as a result of the degeneracy of the genetic code are also a constituent of the invention. In the same way, DNA sequences which hybridize with SEQ ID NO:1 or parts of SEQ ID NO:1 are a constituent of the invention. Conservative amino acid exchanges, such as, for example, the exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C *terminus* of a protein cannot substantially impair or can even stabilize the function thereof. Information in this context can be found by the expert, inter alia, in Ben-Bassat et al. (journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID NO:2 are also a constituent of the invention.

In the same way, DNA sequences which hybridize with SEQ ID NO:1 or portions of SEQ ID NO:1 are a constituent of the invention. Finally, DNA sequences which are prepared by the polymerase chain reaction (PCR) using primers which result from SEQ ID NO:1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). Instructions for amplification of DNA sequences with the aid of the polymerase chain reaction (PCR) can be found by the expert, inter alia, in the handbook by Gait: Oligonucleotide synthesis: a practical approach (IRL Press, Oxford, UK, 1984) and in Newton and Graham: PCR (Spektrum Akademischer Verlag, Heidelberg, Germany, 1994).

The inventors have found that coryneform bacteria produce amino acids, in particular L-lysine, in an improved manner after over-expression of the pfk gene.

To achieve over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine production. The expression is likewise improved by measures to prolong the life of the m-RNA. Furthermore, the enzyme activity is also increased by preventing the degradation of the enzyme protein. The genes or gene constructions can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification EPS 0 472 869, in U.S. Pat. No. 4,601,893, in Schwarzer and PUhler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, the pfk gene according to the invention was over-expressed with the aid of plasmids.

Suitable plasmids are those which are replicated in *coryneform bacteria*. Numerous known plasmid vectors, such as, for example, pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as, for example, those based on pCG4 (U.S. Pat. No. 4,489,160) or pNG2 (Serwold-Davis et al., FEMS Microbiology Letters 66, 119–124 (1990)), or pAG1 (U.S. Pat. No. 5,158,891) can be used in the same manner.

Plasmid vectors which are furthermore suitable are those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pKI8mob or pKI9mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)) or pEMI (Schrumpf et al, 1991, Journal of Bacteriology 173:4510–4516). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of amino acids, in particular L-lysine, to enhance or over-express one or more enzymes of the particular biosynthesis pathway, of glycolysis, of anaplerosis, of the citric acid cycle or of amino acid export, in addition to the pfk gene.

Thus, for example, for the preparation of L-lysine, one or more genes chosen from the group consisting of the dapA gene which encodes dihydrodipicolinate synthase (EP-B 0 197 335), or the gap gene which encodes glyceraldehyde 3-phosphate dehydrogenase (Eikmanns (1992), Journal of Bacteriology 174:6076–6086), or the tpi gene which encodes triose phosphate isomerase (Eikmanns (1992), Journal of Bacteriology 174:6076–6086), or the pgk gene which encodes 3-phosphoglycerate kinase (Eikmanns (1992), Journal of Bacteriology 174:6076–6086), or the pyc gene which encodes pyruvate carboxylase (Eikmanns (1992), Journal of Bacteriology 174:6076–6086), or the lysE gene which encodes lysine export (DE-A-195 48 222)

can be over-expressed at the same time.

For the production of amino acids, in particular L-lysine, it may furthermore be advantageous to attenuate, in addition to the pfk gene, the pck gene which encodes phosphoenol pyruvate carboxykinase (DE 199 50 409.1, DSM 13047) and/or the pgi gene which encodes glucose 6-phosphate isomerase (US 09/396,478, DSM 12969)

at the same time.

In addition to over-expression of the pfk gene it may furthermore be advantageous, for the production of amino acids, in particular L-lysine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of amino acids, in particular L-lysine. A summary of known culture methods is contained in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as, for example, glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of lysine has formed. This target is usually reached within 10 hours to 160 hours.

The analysis of L-lysine can be carried out by anion exchange chromatography with subsequent ninhydrin derivatization, as described by Spackman et al. (Analytical Chemistry, 30, (1958), 1190).

The process according to the invention is used for the fermentative preparation of amino acids, in particular L-lysine

BRIEF DESCRIPTION OF THE DRAWING

FIG. 1: Plasmid pZ-pfkex

The abbreviations used in the figure have the following meaning:

Kan: Resistance gene for kanamycin
Ptac: tac promoter
pfk: pfk gene of *C. glutamicum*
rrnB-T1T2: Terminator T1T2 of the rrnB gene of *E.coli*
rep: Plasmid-coded replication origin for *C. glutamicum* (of pHM1519)
EcoRI: Cleavage site of the restriction enzyme EcoRI
SalI: cleavage site of the restriction enzyme SalI

DETAILED DESCRIPTION OF THE INVENTION

The present invention is explained in more detail in the following with the aid of embodiment examples.

EXAMPLE 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27–0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from the company Stratagene (La Jolla, USA, Product Description SuperCos1 Cosmid Vektor Kit, Code no. 251301) was cleaved with the restriction enzyme XbaI (Amersham Pharmacia, Freiburg, Germany, Product Description XbaI, Code no. 27–0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27–0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-404). The ligation mixture was then packed in phages with the aid of Gigapack II XL Packing Extracts (Stratagene, La Jolla, USA, Product Description Gigapack II XL Packing Extract, Code no. 200217). For infection of the E. coli strain NM554 (Raleigh et al. 1988, Nucleic Acid Research 16:1563–1575).the cells were taken up in mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

EXAMPLE 2

Isolation and Sequencing of the pfk Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from the company Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the E. coli strain DHαMCR (Grant, 1990, Proceedings of the National Academy of Sciences U.S.A., 87:4645–4649) and plated out on LB agar (Lennox, 1955, virology, 1:190) with 50 µg/ml zeocin. The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 37711" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis [sic] were prepared with the XNIP program (Staden, 1986, Nucleic Acids Research, 14:217–231). Further analyses were carried out with the "BLAST search program" (Altschul et al., 1997, Nucleic Acids Research, 25:3389–3402), against the non-redundant databank of the "National Center for Biotechnology Information" (NCBI, Bethesda, Md., USA).

The resulting nucleotide sequence is shown in SEQ ID NO:1. Analysis of the nucleotide sequence showed an open reading frame of 990 base pairs, which was designated the pfk gene. The pfk gene encodes a protein of 330 amino acids.

EXAMPLE 3

Preparation of the Expression Vector pZ-pfkex for Enhancement of the pfk Gene in *Corynebacterium glutamicum*

3.1. Cloning of the pfk Gene

From the strain ATCC 13032, chromosomal DNA was isolated by the method of Eikmanns et al. (Microbiology 140: 1817–1828 (1994)). On the basis of the sequence of the pfk gene known for C. glutamicum from example 2, the following oligonucleotides were chosen for the polymerase chain reaction:

pfk-ex: 5' GAT CTA GAA TTC AAC TTT CAG GTG GTA ACC C 3' (SEQ ID NO:3)

pfk-glp2:

5' GAT CTA GTC GAC COG ACA AGC GAG GAA TTA T 3' (SEQ ID NO:4)

The primers described were synthesized by ARK Scientific GmbH Biosystems (Darmstadt, Germany). The primer pfk-ex contains the sequence for the cleavage site of the restriction endonuclease EcoRI and the primer pfk-glp2 the cleavage site of the restriction endonuclease SalI, which are marked by underlining in the nucleotide sequence shown above. The PCR reaction was carried out by the standard PCR method of Innis et al. (PCR protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment of approx. 1.05 kb in size, which carries the pfk gene from *Corynebacterium glutamicum*. The product amplified in this way was tested electrophoretically in a 0.8% agarose gel.

The PCR fragment obtained in this manner was cleaved completely with the restriction enzymes EcoRI and SalI. The pfk fragment approx. 1.05 kb in size was isolated from the agarose gel with the QiaExII Gel Extraction Kit (Product No. 20021, Qiagen, Hilden, Germany).

3.2. Cloning of pfk in the Vector pZ8-1

The E. coli—C. glutamicum—shuttle—expression vector pZ8-1 (EP 0 375 889) was employed as the base vector for expression both in C. glutamicum and in E. coli. DNA of this plasmid was cleaved completely with the restriction enzymes EcoRI and SalI and then dephosphorylated with shrimp alkaline phosphatase (Roche Diagnostics GmbH, Mannheim, Germany, Product Description SAP, Product No. 1758250). The pfk fragment isolated from the agarose gel in example 3.1 was mixed with the vector pZ8-1 prepared in this way and the batch was treated with T4 DNA ligase (Amersham Pharmacia, Freiburg, Germany, Product Description T4-DNA-Ligase, Code no.27-0870-04).

The ligation batch was transformed in the E. coli strain DHαmcr (Hanahan, In: DNA cloning. A Practical Approach, Vol. I, IRL-Press, Oxford, Washington DC, USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and investigated by restriction cleavage. The resulting plasmid was called pZ-pfkex. It is shown in FIG. 1.

EXAMPLE 4

Transformation of the Strain DSM5715 with the Plasmid pZ-pfkex

The strain DSM5715 was transformed with the plasmid pZ-pfkex using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology 144, 915–927), cleaved with the restriction endonucleases EcoRI and SalI, and the plasmid was checked by subsequent agarose gel electrophoresis. The resulting strain was called DSM5715/pZ-pfkex.

EXAMPLE 5

Preparation of Lysine

The C. glutamicum strain DSM5715/pZ-pfkex obtained in example 4 was cultured in a nutrient medium suitable for the production of lysine and the lysine content in the culture supernatant was determined.

For this, the strain was first incubated on an agar plate with the corresponding antibiotic (brain-heart agar with tetracycline (5 mg/l)) for 24 hours at 33° C. Starting from this agar plate culture, a preculture was seeded (10 ml medium in a 100 ml conical flask). The complete medium Cg III was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamtcin (25 mg/l) was added to this. The preculture was incubated for 16 hours at 33° C. at 240 rpm on a shaking machine. A main culture was seeded from this preculture such that the initial OD (660 nm) of the main culture was 0.05. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660) | Lysine HCl g/l |
|---|---|---|
| DSM5715 | 7.9 | 13.0 |
| DSM5715/pZ-pfkex | 9.9 | 13.4 |

What is claimed is:

1. An isolated nucleic acid comprising a nucleotide sequence selected from the group consisting of:
   (a) a nucleotide sequence as set forth in SEQ ID NO:1; and
   (b) a nucleotide sequence fully complementary to (a).
2. A vector comprising the nucleic acid of claim 1.
3. The vector of claim 2, wherein said vector is a plasmid.
4. The vector of claim 3, further comprising a promoter.
5. A bacterial host cell comprising the vector of claim 2.
6. The bacterial host cell of claim 5 that is of the species *Corynebacterium glutamicum*.

7. A process for the production of an L-amino acid comprising the following steps:
   (a) culturing the bacterial host cell of claim 5 in a suitable culture medium to produce the L-amino acid;
   (b) accumulating said L-amino acid in the culture medium or in the bacterial host cell; and
   (c) isolating the L-amino acid produced thereby.
8. The process of claim 7, wherein the L-amino acid is L-lysine.

* * * * *